US00PP32474P2

(12) United States Plant Patent
Breier

(10) Patent No.: US PP32,474 P2
(45) Date of Patent: Nov. 17, 2020

(54) ***DIANTHUS* PLANT NAMED 'PG-072'**

(50) Latin Name: *Dianthus caryophyllus*
Varietal Denomination: PG-072

(71) Applicant: Ilan Breier, Bnei Zion (IL)

(72) Inventor: Ilan Breier, Bnei Zion (IL)

( * ) Notice: Subject to any disclaimer, the term of this patent is extended or adjusted under 35 U.S.C. 154(b) by 0 days.

(21) Appl. No.: 16/602,145

(22) Filed: Aug. 14, 2019

(51) Int. Cl.
*A01H 5/02* (2018.01)
*A01H 6/30* (2018.01)

(52) U.S. Cl.
USPC ..... Plt./277

(58) Field of Classification Search
USPC ..... Plt./263.1, 272, 273, 277
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Dianthus* cultivar named 'PG-072' is disclosed, characterized by dark pink double flowers, prolific flowering and a cascading, compact habit. The new variety is a *Dianthus*, typically produced as a garden or container plant.

2 Drawing Sheets

Latin name of the genus and species: *Dianthus caryophyllus*.

Variety denomination: 'PG-072'.

BACKGROUND OF THE INVENTION

The new cultivar is a product of planned breeding program by the inventor, Ilan Breier. The objective was to create new varieties of *Dianthus* for hanging baskets. The crossing resulting in this new variety was made during 2012 at a commercial nursery in Bnei Zion, Israel. 'PG-072' was discovered and selected in 2014 by the inventor at the same nursery in Bnei Zion, Israel.

Asexual reproduction of the new cultivar 'PG-072' was first performed in Bnei Zion, Israel by vegetative terminal cuttings in 2014. 'PG-072' has since produced several generations and has shown that the unique features of this cultivar are stable and reproduced true to type.

SUMMARY OF THE INVENTION

The cultivar 'PG-072' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PG-072'. These characteristics in combination distinguish 'PG-072' as a new and distinct *Dianthus* cultivar:

1. Prolific flowering.
2. Dark pink, double flowers.
2. Unique cascading growth habit, suitable for hanging baskets.
3. Compact habit.

PARENTAL COMPARISONS

Plants of the new cultivar 'PG-072' are comparable to the seed parent, *Dianthus* 'PE-58', unpatented, in most horticultural characteristics; however, the new variety 'PG-072' differs in the following:

1. The new variety has a cascading habit, while the seed parent does not.

Plants of the new cultivar 'PG-072' are comparable to the pollen parent, *Dianthus* 'F Line', unpatented, in most horticultural characteristics; however, the new variety 'PG-072' differs in the following:

1. The new variety has a cascading habit, while the pollen parent does not.
2. The new variety is a smaller plant than the pollen parent.

COMMERCIAL COMPARISON

Plants of the new cultivar 'PG-072' are comparable to the commercial *Dianthus* 'Whatfield Magenta', unpatented. The two *Dianthus* varieties are similar in most horticultural characteristics; however, the new variety 'PG-072' differs in the following:

1. The new variety has a cascading habit, while this comparator does not.
2. The new variety has double flowers, while this comparator has single flowers.

BRIEF DESCRIPTION OF THE PHOTOGRAPHS

Figure 1:
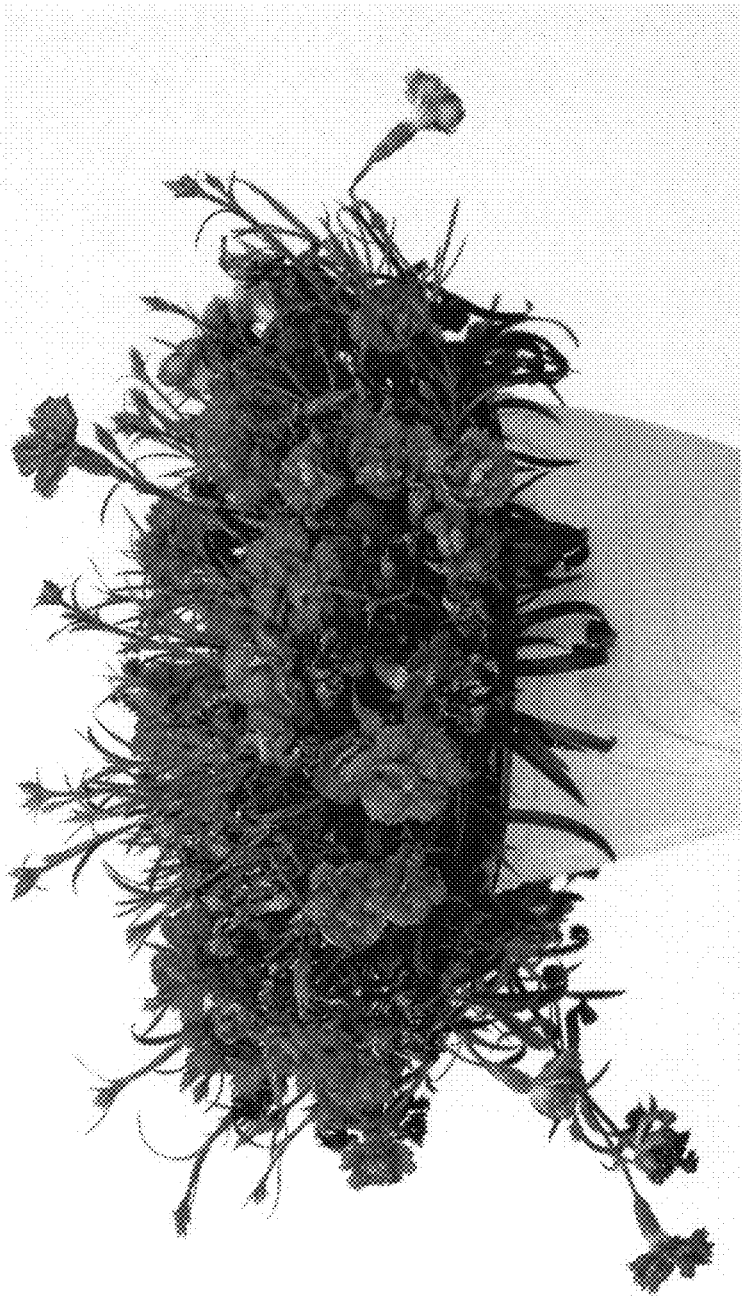

The accompanying photograph in FIG. 1 illustrates in full color a typical plant of 'PG-072' grown outdoors in Bnei Zion, Israel. This plant is approximately 20 weeks old, shown in an 8-inch pot.

Figure 2:
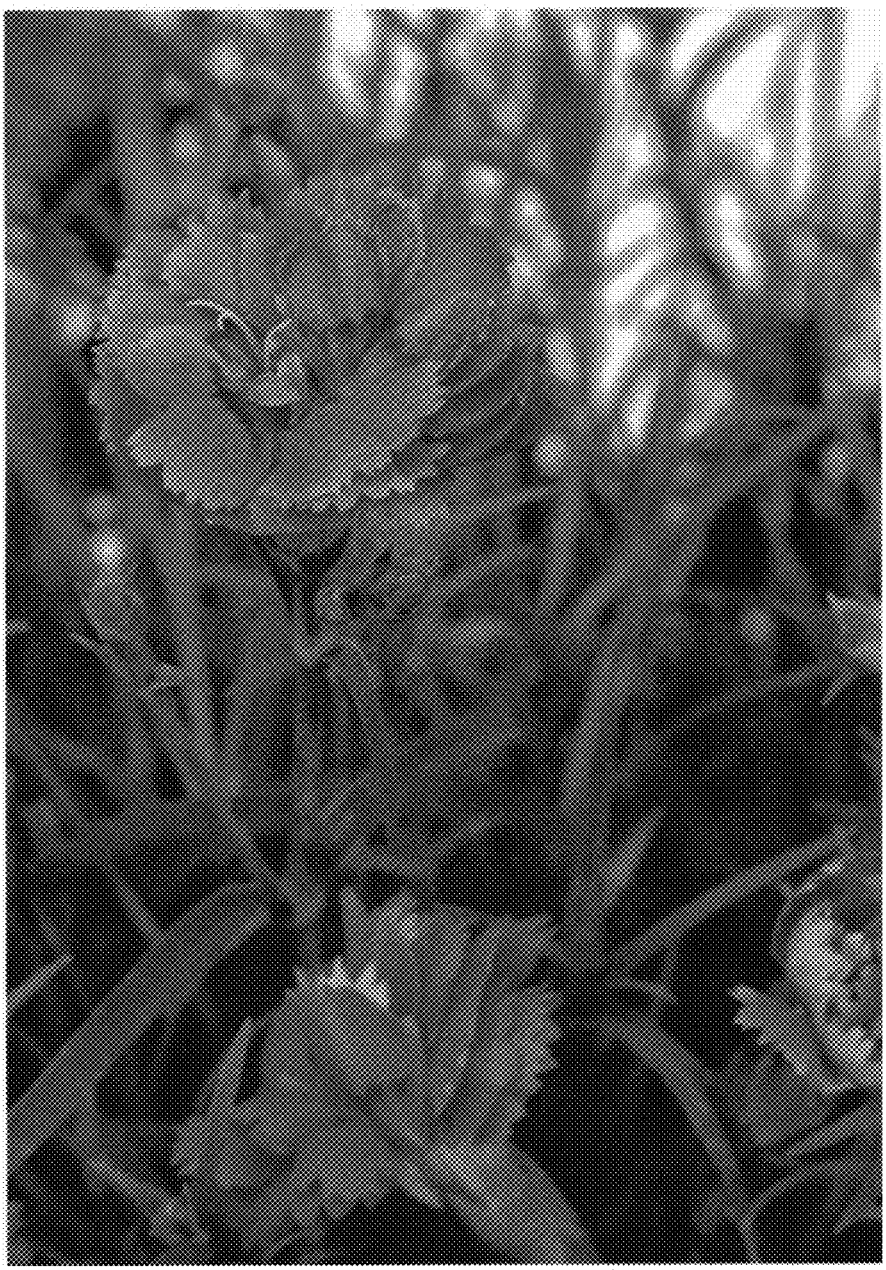

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2015, except where general terms of ordinary dictionary significance are used. The following observations and measurements describe 'PG-072' plants in a commercial greenhouse in Bnei Zion, Israel. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Dianthus caryophyllus* 'PG-072'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near RHS Orange-White 159C.

PLANT

Age of plant described: 24 months.
Pot size: 18 cm circular container.
Plant type: Herbaceous perennial.
Plant habit: Compact.
Growth rate: Moderate.
Plant vigor: Moderate to high.
Plant spread: Average 44.8 cm.
Height: Average 14.7 cm to top of flowering plane; 16.7 cm to top of foliar plane.
Length plant stem: Average 11 cm.
Diameter of plant stem: Approximately 3.0 mm.
Quantity stems: Approximately 30.
Branching habit: Main stems grow from base, with lateral stems.
Basal branching: Present, as well as lateral branches.
Number primary branches: Average 50 per plant.
Number secondary branches: Average 6 per plant.
Lateral branch:
- *Length*.—Average: 14.3 cm.
- *Diameter*.—Average: 0.2 cm.

Internode length: Average 3.1 cm.
Stem:
- *Shape*.—Circular.
- *Aspect*.—Towards all directions.
- *Strength*.—Strong.
- *Luster*.—Moderately glossy, but covered with a very thin and matte waxy layer.
- *Color*.—Developing: RHS Yellow-Green 145B. At Internodes: RHS Yellow-Green 145C. Developed: RHS Green NN137A, covered with a very thin waxy layer, Green 136B. Oldest stems: RHS Greyed-Orange 165B.
- *Pubescence*.—None.

FOLIAGE

Leaf:
- *Arrangement*.—Opposite, single.
- *Quantity*.—Approximately 10-12 fully expanded per stem. Average range of 10-12 immature leaves per stem.
- *Average length*.—10.2 cm.
- *Average width*.—0.5 cm.
- *Shape of blade*.—Narrow oblanceolate to linear, slightly carinate, moderately curled.
- *Apex*.—Acute.
- *Base*.—Decurrent.
- *Margin*.—Entire.
- *Texture of top surface*.—Smooth, glabrous.
- *Texture of bottom surface*.—Smooth, glabrous.
- *Pubescence*.—None.
- *Rugosity*.—Both sides non-rugose.
- *Luster*.—Upper side: Matte. Under side: Very slightly glossy, main vein glossy.
- *Color*.—Young foliage upper side: Near RHS Green 137B to 137 C. Young foliage under side: Near RHS Green 137C. Mature foliage upper side: Near RHS Green NN137A. Mature foliage under side: Near RHS Green NN137B.
- *Venation*.—Pattern: Parallel. Venation color upper side: RHS Green NN137A. Venation color under side: RHS Green 143A.

Petiole: None.

FLOWER

Natural flowering season: Spring to late Summer.
Type and form: Rotate, double.
Inflorescence type and habit: Solitary or in pairs.
Flower longevity on plant: Average 10 days.
Quantity of flowers: Approximately 80.
Flowers persistent or self-cleaning: Self-cleaning.
Fragrance: Faint and pleasant.
Individual flower size:
- *Diameter*.—Approximately 3.7 cm.
- *Length*.—Approximately 3.3 cm.

Petals:
- *Petal arrangement*.—Rotate.
- *Shape*.—Spatulate.
- *Tip*.—Irregular toothed and praemorse.
- *Base*.—Narrow cuneate.
- *Margin*.—Irregular dentate, lower half entire.
- *Margin undulation*.—Medium.
- *Length*.—Average 3.6 cm.
- *Width*.—Average 1.6 cm.
- *Petal quantity*.—Average range 20 to 25.
- *Texture, upper side*.—Velvety, glabrous.
- *Texture, under side*.—Slightly velvety, glabrous.
- *Rugosity*.—Both sides non-rugose.
- *Aspect*.—Flat to slightly undulating.
- *Color*.—When opening: Upper surface: RHS Purple N78A, blotched 71A and N79C at the base of the broad part of the petal; base Yellow-Green 145D. Lower surface: RHS Red-Purple N74C, veined Yellow-Green 145D, base Yellow-Green 145D. Fully opened: Upper surface: RHS Purple NN78A, blotched N79C and slightly darker at the base of the broad part of the petal; base yellow-green 145D. Lower surface: RHS Red-Purple N78B, fading to N78D towards the base of the broad part of the petal; base Yellow-Green 145D. Fading: Not fading.

Petaloids:
- *Arrangement*.—Rotate.
- *Number per flower*.—Average 16.
- *Number of whorls*.—Average 3.
- *Fused*.—No.
- *Shape*.—Spatulate.
- *Length*.—Average: 3.4 cm.

*Width*.—Average: 1.4 cm.
*Tip*.—Irregular toothed and praemorse.
*Base*.—Narrow cuneate.
*Margin*.—Irregular dentate, lower half entire.
*Margin undulation*.—Medium.
*Texture, upper side*.—Velvety.
*Texture, under side*.—Slightly velvety.
*Rugosity*.—Both sides non-rugose.
*Luster*.—Both sides matte.
*Color*.—When Opening: Upper Side: RHS Purple N78A, blotched at the base of the broad part of the petal, in between Purple 71A and Red-Purple N79C, base Yellow-Green 145D. Under Side: RHS Red-Purple N74C, veined Yellow-Green 145D, base Yellow-Green 145D. Fully Opened: Upper Side: RHS Purple NN78A, blotched Purple N79C at the base of the broad part of the petal, and slightly darker; base Yellow-Green 145D. Under Side: RHS Red-Purple N78B, fading lighter towards the base of the broad part of the petal, Red-Purple N78; base Yellow-Green 145D. Fading: Not fading.

Bud:
*Shape*.—Elliptic.
*Length*.—Average 1.6 cm.
*Diameter*.—Average 0.6 cm.
*Color*.—RHS Green 143B, base Yellow-Green 145B.

Sepals:
*Quantity*.—5.
*Arrangement*.—Rotate, fused into campanulate shape.
*Shape*.—Oblong.
*Length*.—1.6 cm.
*Width*.—0.45 cm.
*Margin*.—Entire.
*Apex*.—Acute.
*Texture*.—Smooth, glabrous, upper and lower surfaces.
*Color*.—RHS Yellow-Green 144B.

Peduncle: None present; flowers solitary.

Pedicel:
*Length*.—Average 1.1 cm.
*Diameter*.—Average 0.15 cm.
*Color*.—Near RHS Green 137A.
*Angle*.—Average angle to stem axis: 20°.
*Strength*.—Moderately strong.

REPRODUCTIVE ORGANS

Stamens:
*Number*.—Average 5; deformed stamen.
*Filament length*.—Approximately 0.3 cm.

Anthers:
*Shape*.—Narrow elliptic to narrow sagittate, dorsifixed.
*Length*.—Approximately 0.15 cm.
*Width*.—Average 0.05 cm.
*Color*.—RHS Greyed-Yellow 161D.
*Pollen*.—Not observed.

Pistil:
*Number*.—Average 2.
*Length*.—Approximately 2.3 cm.
*Style*.—Length: Approximately 2.2 cm. Color: Near RHS White N155D.

Stigma:
*Shape*.—Pointed, curved.
*Color*.—Near RHS White N155C.
*Ovary color*.—RHS Yellow-Green 144C to 144D.

OTHER CHARACTERISTICS

Seeds and fruits: Not observed to date.

Disease/pest resistance: Neither resistance nor susceptibility to the normal diseases and pests of *Dianthus* has been observed. Typical diseases of *Dianthus* include: *Alternaria dianthicola, Botrytis cinerea, Erwinia chrysanthemi, Pseudomonas caryophylli, Fusarium graminearum, Fusarium avenaceum, Fusarium culmorum* and *Rhizoctonia solani*, Typical pests include; various species of *Thysanopthera*, various *Aphis* species, and various species of *Tetranychus*.

Temperature tolerance: USDA zones 3 through 10 tolerant.

What is claimed is:

1. A new and distinct cultivar of *Dianthus* plant named 'PG-072' as herein illustrated and described.

* * * * *